United States Patent [19]

Schmitt

[11] 4,155,992
[45] May 22, 1979

[54] PHARMACEUTICAL COMPOSITION OF POLY(ORTHOESTER) CO- AND HOMOPOLYMERS AND POLY(ORTHOCARBONATE) CO- AND HOMOPOLYMERS HAVING CARBONYLOXY FUNCTIONALITY WITH DRUG

[75] Inventor: Edward E. Schmitt, Palo Alto, Calif.

[73] Assignee: Alza Corporation, Palo Alto, Calif.

[21] Appl. No.: 843,750

[22] Filed: Oct. 19, 1977

Related U.S. Application Data

[62] Division of Ser. No. 714,577, Aug. 16, 1976, Pat. No. 4,070,347.

[51] Int. Cl.$^2$ .......................... A61K 9/22; A61K 9/32; A61K 9/58; A61K 31/765
[52] U.S. Cl. .................................. 424/19; 424/20; 424/32; 424/78
[58] Field of Search .................. 424/19, 20, 78, 32

[56] References Cited

U.S. PATENT DOCUMENTS

| | | | |
|---|---|---|---|
| 3,914,402 | 10/1975 | Shell | 424/32 |
| 3,983,209 | 9/1976 | Schmitt | 424/78 |
| 4,001,388 | 1/1977 | Shell | 424/20 |
| 4,070,347 | 1/1978 | Schmitt | 424/78 |
| 4,093,709 | 6/1978 | Choi et al. | 424/19 |

Primary Examiner—Donald B. Moyer
Attorney, Agent, or Firm—Paul L. Sabatine; Tom E. Ciotti; Edward L. Mandell

[57] ABSTRACT

Poly(orthoester) co- and homopolymers and poly(orthocarbonate) co- and homopolymers comprising (1) a repeating dioxycarbon unit in the polymeric backbone having a plurality of organic groups pendant therefrom, and (2) a bridging moiety having at least one carbonyloxy group contained therein are disclosed. The polymers are represented by the formula:

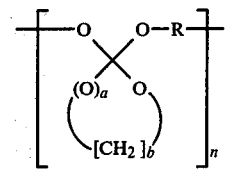

wherein R is a bridging moiety and is either $R_1$ or $R_2$ arranged in a random manner along the polymeric backbone to form a copolymer containing both $R_1$ and $R_2$ with $R_1$ an aliphatic, an alicyclic or an aromatic group and $R_2$ is a

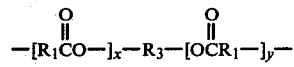

group with $R_1$ as defined and $R_3$ an aliphatic, an alicyclic or aromatic group, or wherein R is a bridging moiety and is only $R_2$ to form a homopolymer with $R_1$, $R_2$, and $R_3$ as defined above, and a is 0 to 1, b is 2 to 6, and n and the sum of x and y are positive integers. The copolymers are useful for making articles of manufacture, including devices and coatings for delivering beneficial agents.

1 Claim, 1 Drawing Figure

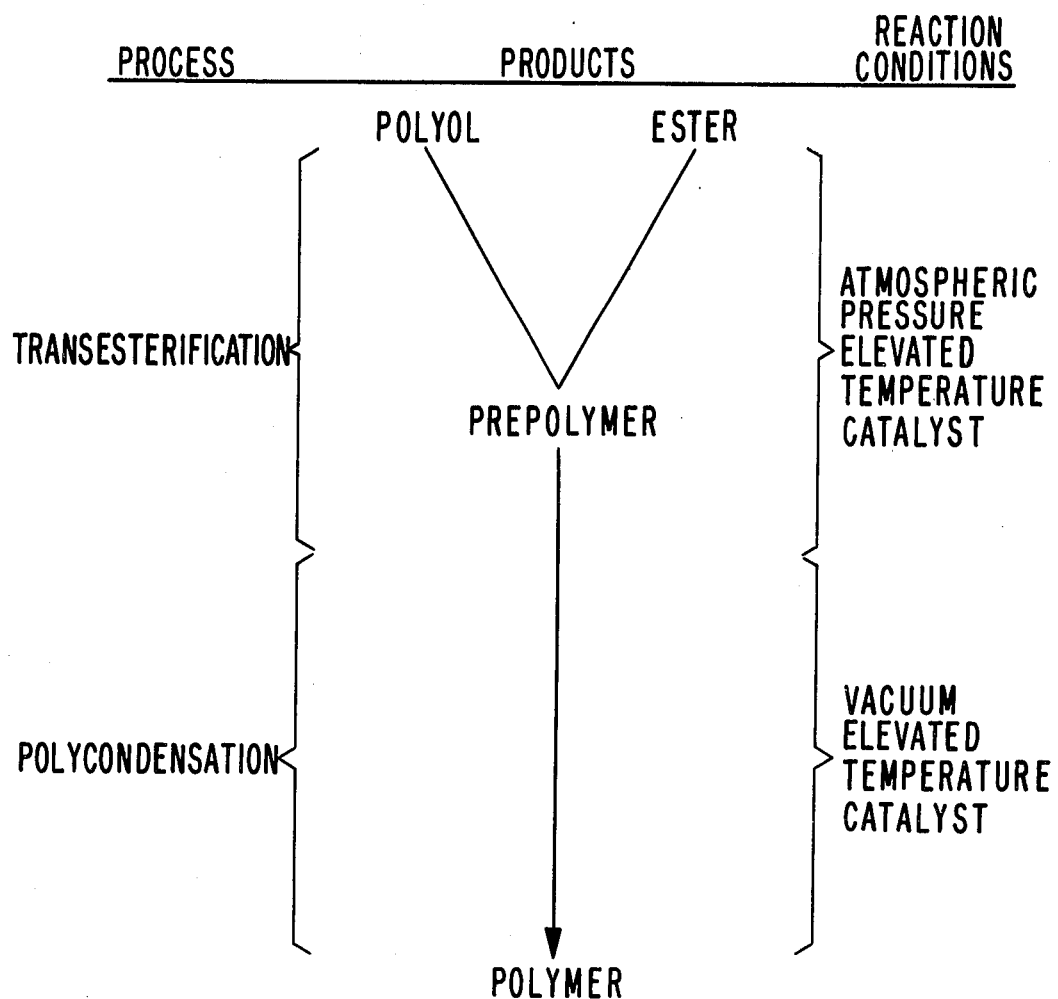

PHARMACEUTICAL COMPOSITION OF POLY(ORTHOESTER) CO- AND HOMOPOLYMERS AND POLY(ORTHOCARBONATE) CO- AND HOMOPOLYMERS HAVING CARBONYLOXY FUNCTIONALITY WITH DRUG

CROSS-REFERENCE TO RELATED APPLICATION

This application is a division of application U.S. Ser. No. 714,577 filed on Aug. 16, 1976 now U.S. Pat. No. 4,070,347 issued on Jan. 24, 1978, which Ser. No. 714,577 is incorporated herein by reference and benefit of Ser. No. 714,577 filing date is claimed herein. This application is copending with U.S. Application Ser. No. 544,808 filed Jan. 28, 1975 now U.S. Pat. No. 4,093,709 issued on June 6, 1978 by N. Choi and J. Heller, which application disclosed orthoester and orthocarbonate polymers comprising a polymeric backbone having a dioxycarbon unit with a multiplicity of hydrocarbon groups bonded thereto. The polymers of Choi and Heller have both oxygens of the dioxycarbon backbone formed independently of a heterocyclic ring, while the polymers of the present invention have coupled with the orthoester or orthocarbonate an unobvious structure benefit of a structurally different polyester sequence in the polymeric backbone. These applications are assigned to the same assignee of this application.

BACKGROUND OF THE INVENTION

The present invention relates to co- and homopolymers. More particularly, the invention pertains to novel and useful co- and homopolymers comprising (1) a dioxycarbon unit in the polymer backbone having a plurality of organic groups pendant therefrom, and (2) a bridging moiety having at least one carbonyloxy group contained therein. The copolymers of the invention are represented by the following general formula:

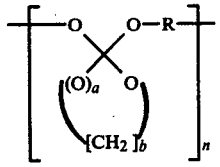

wherein R is a bridging moiety and is either $R_1$ or $R_2$ arranged in a random manner along the polymeric backbone to form a copolymer containing both $R_1$ and $R_2$. The homopolymers of the invention are represented by the same general formula but wherein R is only $R_2$. In the formula, $R_1$ is a member selected from the group consisting of alkylene; alkenylene; cycloalkylene; cycloalkylene substituted with a member selected from the group consisting of alkyl, alkenyl, alkoxy and alkylene; cycloalkenylene; and cycloalkenylene substituted with a member selected from the group consisting of alkyl, alkenyl, alkoxy and alkylene; arylene; and arylene substituted with a member selected from the group consisting of alkyl, alkenyl, alkoxy and alkylene. $R_2$ is

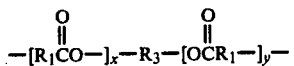

wherein $R_1$ is as defined and $R_3$ is a member selected from the group consisting of alkylene; alkenylene; cycloalkylene; cycloalkylene substituted with a member selected from the group consisting of alkyl, alkenyl, alkoxy and alkylene; cycloalkenylene, cycloalkenylene substituted with a member selected from the group consisting of alkyl, alkenyl, alkoxy and alkylene; and arylene; and arylene substituted with a member selected from the group consisting of alkyl, alkenyl, alkoxy and alkylene; a is 0 to 1; b is 2 to 6; x and y are independently 0 to 100 with the proviso that one of x and y is a positive whole integer of at least one and n is at least 10, usually 10 to 1000. The copolymers of the invention include copolymers of the random and block types formed by reacting monomers of preformed homopolymers, prepolymers, copolymers or oligomers, and noncrosslinked and cross-linked polymers.

DESCRIPTION OF THE PRIOR ART

The reaction of orthoesters with glycols leading to non-polymeric and other diverse products is known to the art in the references such as *Ind. J. Appl. Chem.*, Vol. 28, No. 2, pages 53 to 58, 1965, wherein Mehrota, et al obtained monoethoxy-monoglycolate and triglycoxy-bisorthoformate by reacting orthoformate with hexamethylene glycol in molar ratios of one to one and two to three to yield low molecular weight compounds. Similarly, Crank, et al in *Aust. J. Chem.*, Vol. 17, pages 1392 to 1394, 1964, disclosed the reaction of triols with orthoesters including ethyl orthoformate with butane 1,2,4-triol, pentane-1,2,5-triol and pentane-1,3,5-triol to form monomeric bicyclic compounds. During the preparation of the bicyclic orthoesters by reacting ethyl orthoformate with triols, Crank, et al found that compounds produced from starting materials having a 1,2-diol structure also contained compounds having ethylene linkages. In a subsequent paper, Crank, et al *Aust. J. Chem.*, Vol. 17, pages 1934 to 1938, 1964, developed this reaction into a synthetic procedure for the conversion of 1,2-diols into olefins. Later, DeWolfe in *Carboxylic Ortho Acid Derivatives*, 1970, published by Academic Press, Inc., New York, noted that carboxylic orthoesters are more reactive toward acid hydrolysis than almost any other class of compounds, and this high hydrolytic reactivity complicates their synthesis and storage. DeWolfe reported that the conversion of diols to cyclic orthoesters including alkoxydioxolane or alkoxydioxane, followed by acid hydrolysis, provides a method for monoacylating diols. More recently, Bailey reported in *Polym. Prepr. Amer. Chem. Soc. Div. Polym. Chem.*, Vol. 13, No. 1, pages 281 to 286, 1972, that the polymerization of spiro orthoesters at ambient and elevated temperatures led to polyesters and polycarbonates of the structures [—$CH_2CH_2CH_2COOCH_2CH_2O$—]$_n$ and [—$OCH_2OCOOCH_2CH_2CH_2$—]$_n$. The process for preparing the polyglycolic acid is a well-known process in the art as shown in U.S. Pat. No. 2,668,162, Lowe, "Preparation of High Molecular Polyhydroxy-acetic Esters," and the U.S. Pat. No. 2,676,945, Higgins, "Condensation Polymers of Hydroxy-acetic Acid." Polymers of lactic acid have been produced by self-esterification with elimination of water in U.S. Pat. No. 2,703,316, Schneider, "Polymers of High Melting Lactide."

SUMMARY OF THE INVENTION

The invention concerns a new class of linear backbone co- and homopolymers having a repeating unit comprising hydrocarbon radicals containing at least one carbonyloxy group and a symmetrical dioxycarbon unit with a plurality of organic groups pendant from the carbon atom. The oxycarbonyl ester moiety is covalently bonded to the oxygen of the dioxycarbon through a hydrocarbyl having a bivalent functionality. The co- and homopolymers of the invention possess a controllable degree of hydrophobicity, which property lends the polymers for use in aqueous and aqueous-like environments where controlled erosion of the polymers to innocuous products is desired. The co- and homopolymers are useful as coatings for the protection of beneficial agent, and for forming delivery devices with drug dispersed therein for their release to a preselected environment by controlled polymeric erosion over a prolonged period of time.

DETAILED DESCRIPTION OF THE INVENTION

The expressions "aliphatic", "alicyclic" and "aromatic" appearing above and as used in this specification, include, for the purpose of this invention, the terms embraced by $R_1$ and $R_3$ as defined below.

The term "alkylene" used in this specification for $R_1$ and $R_3$ denotes straight and branched chain divalent alkylene radicals and the conventionally positioned isomers thereof having 1 to 10 carbon atoms inclusive, such as methylene; 1,2-ethylene; 1,3-propylene; 1,1-propylene; 1,4-butylene; 1,5-pentylene; 2,5-hexylene; 1,6-hexylene; 1,7-heptylene; 2-methyl-1,7-heptylene; 1,8-octylene; 3-isopropoxy-1,7-heptylene; 1,10-decylene; 2-methyl-1,4-butylene; 2-propyl-1,6-hexylene; 1,1-dimethyl-1,6-hexylene; and the like.

The term "alkenylene" as used herein denotes a straight or branched chain divalent radical having 2 to 10 carbon atoms, such as 1,3-prop-1-enylene; 1,4-but-1-enylene; 1,4-but-2-enylene; 1,5-pent-1-enylene; 1,6-hex-2-enylene; 1,7-hept-2-enylene; 1,8-oct-2-enylene; 1,9-non-2-enylene; 4-propyl-(1,6-hex-2-enylene); 5-methoxy-(1,6-hex-2-enylene); 2-propenyl-(1,6-hex-4-enylene); and the like.

The term "cycloalkylene" as used herein for $R_1$ and $R_3$ includes monocyclic, divalent lower cycloalkylene radicals of 3 to 7 carbons such as cyclopropylene, cyclobutylene, cyclopentylene, cyclohexylene and cycloheptylene. Similarly, the phrase "cycloalkylene substituted with an alkyl, alkoxy, alkenyl or alkylene" includes substituted cycloalkylenes such as 2-methyl-1,3-cyclopropylene, 2-methyl-1,4-cyclopentylene, 2-methyl-1,6-cyclohexylene, 2-ethoxy-2,3-cyclopropylene, 5-butoxy-1,4-cyclopentylene, 2-methoxy-1,4-cyclohexylene, 2-propenyl-1,5-cyclopentylene, 2-isobutenyl-1,6-cyclohexylene, 1,4-cyclohexyldimethylene, 1,4-cyclohexyldihexylene, and the like.

Exemplary cycloalkenylene and cycloalkenylene substituted with an alkyl, alkoxy, alkenyl or alkylene include divalent monocyclicalkenylene containing from 5 to 7 carbon atoms as ring members such as 1,4-cyclopent-2-enylene, 1,5-cyclopent-3-enylene, 1,6-cyclohex-2-enylene, 1,6-cyclohex-2-enylene, 5-methyl-(1,4-cyclopent-2-enylene), 6-ethyl-(1,4-cyclohex-2-enylene), 6-ethoxy-(1,5-cyclohex-2-enylene), 2-propyl-(1,5-cyclohex-3-enylene), 2-methoxy-(1,4-cyclohex-2-enylene), 2-methoxy-(1,4-cyclohept-2-enylene), 1,4-cyclohex-2-enyldimethylene, and the like.

The term "arylene" as used herein embraces 6 to 20 carbons and it includes benzoid arylene, fused benzoid arylene, and arylene and fused arylene groups substituted with an alkyl, alkenyl, alkoxy or alkylene such as phenylene, phenylalkylene, phenylalkenylene, 1,4-phenylene, 1,4-phenyldimethylene, 1,4-phenyldiethylene, 2-methyl-1,4-phenylene, 2,5-diethyl-1,4-phenylene, and the like.

The term alkyl appearing herein embraces straight and branced chain alkyl radicals of 1 to 10 carbon atoms such as methyl, ethyl, n-propyl, n-butyl, n-amyl, n-hexyl, n-heptyl, n-decyl, and the various positional isomers thereof such as isopropyl, isobutyl, t-butyl, sec-butyl, isoamyl, isohexyl, t-heptyl, and the like.

Exemplary alkenyls as used in the instant application include the straight and branched chain lower alkenyl groups of 2 to 10 carbons such as 1-propenyl, 2-propenyl or allyl, 1-butenyl, 2-butenyl, 1-pentyl, 2-hexenyl, and the corresponding positional isomers thereof, such as 1-isobutenyl, 2-isobutenyl, 2-sec-butenyl, 2-methyl-1-butenyl, 2-methyl-2-pentenyl, 2,3-dimethyl-3-hexenyl, and the like.

The term "alkoxy" used by this invention includes the straight and branched chain lower alkoxy groups and the positional isomers thereof having 1 to 7 carbon atoms inclusive. For example, alkoxy includes methoxy, ethoxy, propoxy, butoxy, n-pentoxy, n-hexoxy, isopropoxy, 2-butoxy, isobutoxy, 3-pentoxy, and the like.

The novel and useful copolymers of the invention are synthesized by first preparing a prepolymer by intimately contacting and reacting at least one polyol with at least one starting compound of the general formula:

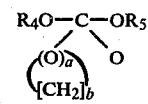

wherein $R_4$ and $R_5$ are defined below to yield the corresponding prepolymer. A detailed description of the total synthesis appears below.

Exemplary polyols suitable as starting reactant monomer include diols, triols, and the like, that can enter into the polymerization reaction to yield the prepolymer without adversely effecting it or the copolymeric product. The polyols used for the purpose of the invention are known to the art, or they can be easily prepared by known organic reactions. Generally, they include $\alpha,\omega$-aliphatic diols, lactide-glycol adducts, glycolide-glycol adducts, triols, and the like, of the straight or branched chain type. Representative polyols are alkane polyols having a terminal hydroxyl group at the terminus of an alkylene chain of 3 to 12 carbon atoms. The non-terminal carbons of the alkylene chain also can bear a hydroxyl group. Typical diols include compounds of the formula $HO-R_6(OH)_c-OH$ wherein $R_6$ is alkylene of 3 to 12, c is 0 to 6, include diols named as glycols such as 1,5-pentylene glycol; 1,6-hexylene glycol; 1,7-heptylene glycol; 1,8-octylene glycol; 1,9-nonylene glycol; 2,3-dimethylene-1,6-hexylene glycol; 3,6-diethyl-1,9-nonylene glycol; and 1,12-dodecamethylene glycol.

Polyols containing more than 2 reactive hydroxyl radicals that can be used for the present purpose include polyhydroxyl compounds such as 1,2,3,4,5,6-hexanehexol; 1,2,3-propanetriol; 1,2,5-pentanetriol; 1,3,5-pentanetriol; 1,2,4-butanetriol; 2-methyl-1,2,3-propanetriol; 2-methyl-2(hydroxymethyl)-1,2-propanediol; 1,4,7-heptanetriol; 1,5,10-decanetriol; 1,5,12-dodecanetriol; pentaerythritol; dipentaerythritol; and $\beta$-methylhlycerol.

Polyols suitable for the purpose of the invention also include polyglycols containing a repeating glycol monoether moiety of the formula $-OCH_2(CH_2)_pOH$ wherein p is 1 to 5, and the polyglycols are diglycols, triglycols, and tetraglycols. Typical polyglycols include diethylene glycol; triethylene glycol; tetraethylene glycol; bis(4-hydroxybutyl)ether; bis(4-hydroxyhexyl)ether; and bis(3-hydroxypropyl)ether.

Additional polyols that can be used include 1,4-cyclohexane dicarbinol as the cis or trans isomeric configuration or mixtures thereof; 2,2,4,4-tetramethyl cyclobutane 1,3-diol; 1,4-(methoxycyclohexane) dicarbinol; 1,4-(3-ethylcyclohexane) dicarbinol; adonitol; mannitol; trimethylol propane; sorbitol; penacol; 2-methyl-1,4-cyclohexane dicarbinol; 3-isopropoxy-1,4-cyclohexane dipropanol; 2-ethyl-1,3-cyclopentane dicarbinol; 1,4-phenyl-dicarbinol; 2-propyl-1,4-phenyl-diethanol; 3-butoxy-1,4-phenyldibutanol; 2,3-dimethyl-1,4-benzylol; 1,3-cyclopropanol; 1,6-hex-2-enylenegl; and 2-propenyl-1,4-cyclohexane dipropanol.

The starting polyols also include lactide alkylene glycol adducts, glycolide alkylene glycol adducts, intermolecular cyclic ester lactide glycol adducts and intramolecular cyclic ester lactone glycol adducts wherein the polyol is obtained by reacting a polyhydroxyl compound with a glycolide, a lactide, a lactic acid derivative or glycolic acid derivative such as glycolide, β-proprolactone, tetramethylglycolide, β-butyrololactone, trimethylglycolide, γ-butyrolactone, pivalolactone, α-hydroxybutyric acid, α-hydroxyiso-butyric acid, α-hydroxyvaleric acid, α-hydroisovaleric acid, α-hydroxycaproic acid, α-hydroxyethylbutyric acid, α-hydroxyisocaproic acid, α-hydroxy-heptanoic acid, α-hydroxy-octanoic acid, α-hydroxystearic acid, α-hydroxylignocenic acid, β-phenyl lactic acid, 1,4-bis(-hydroxymethyl)cyclohexyl 4-hydroxybutyrate, 1,4-bis(hydroxyethyl)cyclohexyl 4-hydroxybutyrate, and the like. Also, the reactive ols glycolide hexamethylene diol, glycolide ethylene glycol oligomer, caprolactone hexamethylene diol and caprolactone cis/transcyclohexane dimethanol. The preparation of the above polyols is well known to the art in *Acta Pharm. Jugaslav.*, Vol. 2, pages 134 to 139, 1952; *Ann.*, Vol. 594, pages 76 to 88, 1955; *J. Am. Chem. Soc.*, Vol. 71, pages 3618 to 3621, 1949; ibid., Vol. 74, pages 2674 to 2675, 1952; *Chem. Abst.*, Vol. 42, pages 8774 to 8775, 1949; ibid., Vol. 43, pages 571 to 573, and 6652, 1949; ibid., Vol. 44, pages 2554 and 7231, 1950; ibid., Vol. 46, page 9585, 1952; ibid., Vol 47, pages 7575, 1953; ibid., Vol. 48, page 106, 1954; ibid., Vol. 49, pages 6098 to 6099, 1955; *Encyclopedia of Chemical Technology*, Kirk-Othmer, Vol. 10, pages 638 to 678, 1966, published by Interscience Publishers, New York; U.S. Pat. Nos. 2,683,136 and 3,531,561.

Exemplary starting monomers, orthoester and orthocarbonate type, include monomers of the formula

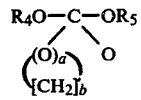

which include compounds that can react in the polymerization synthesis to yield the prepolymers without adversely effecting the reaction or the product. These monomers are known to the art or they can easily be prepared by known organic synthesis. Generally, $R_4$ and $R_5$ are independently the same or different, and they are selected from the group consisting of alkyl and alkenyl as defined hereinafter. The monomer can be a simple or mixed orthoester including saturated and unsaturated orthoesters, such as 2,2-dialkoxy-tetrahydrofuran; 2,2-dialkenyloxy-tetrahydrofuran; 2,2-dialkoxy-dihydrofuran; 2,2-dialkenyloxy-dihydrofuran; 2,2-dialkoxypyran; 2,2-dialkoxy-1-oxepane; 2,2-dialkenyl-1-oxepane; 2,2-dialkoxy-1-oxapane; 2,2-dialkenyloxy-1-octane; 2,2-dialkoxy-1,3-dioxolane; 2,2-dialkenyloxy-1,3-dioxolane; 2,2-dialkoxy-1,3-dioxanes; 2,2-dialkoxy-1,3-dioxonane; and the like.

Examples of the above monomers include 2,2,5-trimethoxy-3,4-dihydrofuran; 2,2-dimethoxy-1,3-dioxolane; 2,2-diethoxy-1,3-dioxolane; 2,2-dipropoxy-1,3-dioxane; 2,2-diethoxy-keto-1,3-dioxane; 2,2-diethoxy-5,5-dimethylpyran; 2,2-diethoxy-5-methyl-tetrahydrofuran; 2,2-diethenyloxy-5-methyl-tetrahydrofuran; 2,2-diethenyloxy-1,3-dioxolane; 2,2-dipropoxy-1-oxopane; 2,2-dibutoxy-1-ocane; 2,2-diethenyloxy-1-oxopane; 2-ethoxy-2-propoxy-1-ocane; 2-isopropoxy-2-ethoxy-1,3-dioxonane; 2-ethoxy-2-propenyloxy-1,3-dioxane; and the like.

The above esters and like esters can be prepared according to the following preparations: The Pinner synthesis as described in *Ber.*, Vol. 16, pages 352 to 363, 1883; and ibid., pages 1644 to 1663, 1883, wherein an appropriate nitrite is reacted with an equivalent amount of dry hydrogen halide and an equivalent amount of alcohol to form an iminoester hydrohalide. This is then alcoholized with an excess of alcohol to form the orthoester. The preparation of orthoesters including the ring type, are known to the art with ample description of the various methods of preparation disclosed in U.S. Pat. Nos. 2,409,699; 2,867,667; 3,323,923; and 3,546,188; and in British Patent Nos. 853,405; and 1,099,559. Also, as found in *Synthetic Organic Chemistry*, Chapter 16, pages 542 to 545, 1953, published by John Wiley and Sons; in *The Chemistry of Aliphatic Orthoesters*, Chapter 2, pages 11 to 43, 1943, Reinhold Publishing Corp.; in *Encyclopedia of Chemical Technology*, Kirk-Othmer, Vol. 8, pages 365 to 383, 1965, Interscience Publishers, New York; *Recueil Trav. Chem. Pays. Bes*, Vol. 88, pages 897 to 904, 1909; *J. Am. Chem. Soc.*, Vol. 64, pages 1825 to 1927, 1942; *Ind. Eng. Chem. Prod. Res. Develop.*, Vol. 10, No. 4, pages 425 to 428, 1971; *J. Am. Chem. Soc.*, Vol. 71, pages 40 to 46, 1949; *Ann. Chem.*, Vol. 675, page 142, 1964; *Agnew. Chem.*, Vol. 69, page 371, 1957; *J. Am. Chem. Soc.*, Vol. 76, pages 5736 to 5739, 1954; ibid., Vol. 44, pages 5601 to 5606, 1955; *Chem. Ber.*, Vol. 89, page 2060, 1956; *Aust. J. Chem.*, Vol. 17, pages 1385 to 1398, 1964; *Gazz. Chem. Ital.*, Vol. 96, page 1164, 1966; *Chem. Commum.*, page 13, 1967; and, *Carboxylic Ortho Acid Derivatives*, Chapter 1, page 1 to 133, 1970, published by Academic Press, New York. The orthoesters can also be prepared by conventional techniques including alcoholysis, condensation, elimination, and reduction reactions, as described in *Organic Functional Group Preparations*, by Sandler and Karo, Vol. II, Chapter 2, pages 41 to 68, 1971, published by Academic Press.

The novel co- and homopolymers of the invention are synthesized by intimately contacting and reacting a monomer polyol including lactide diols, glycolide diols and oligomer diols, with a monomer ester to yield the corresponding prepolymer polymer. Generally, the polymerization reaction is carried out by reacting stoichiometric amounts or an excess thereof, of each starting monomer to yield the polymer. That is, the amount of each reactive monomer can be from about 1 to 10 moles of polyol to 1 to 10 moles of ester monomer, and the like. The polymerization of the monomers is carried out in a suitable reactor vessel, preferably in the presence of a catalyst with continuous mixing of the reactants. The polymerization comprises an initial transesterification reaction followed by a polycondensation reaction with the complete polymerization performed at a temperature of 75° C. to 200° C. over a total reaction time of 2 hours to 96 hours or longer. The transesterification step of the reaction consists of contacting and reacting the monomers with stirring at 125° C. to 180° C. for 2 to 12 hours under normal atmospheric pressure. Then, while maintaining the temperature, the polycondensation reaction is carried out at a reduced pressure of 0.10 to 0.01 mm of mercury for 12 to 96 hours to yield the polymer. The reaction procedure is illustrated in the accompanying flow chart.

The polymer is recovered from the reaction vessel by conventional isolation and recovery techniques. In one embodiment, the polymer is isolated from the reactor while still hot by extruding, or pouring. In another recovery embodiment, the product after cooling, can be dissolved in a suitable organic solvent such as benzene, carbon tetrachloride, methylene chloride, dioxane, toluene, or xylene, followed by the addition thereto of an organic liquid in which the polymer is insoluble, or has limited solubility to precipitate the product. Typical organic liquids for this latter purpose include ether, hexane, pentane, petroleum ether, and hexane heptane mixtures. The product is isolated by filtering and drying under anhydrous conditions. Other methods for recovering the product include lyophizing from a solvent. A flow diagram of the polymerization process is set forth in the accompanying Figure.

Representative catalysts for performing the polymerization reaction are Lewis acids such as boron trifluoride, boron trichloroetherate, boron trifluoride etherate, stannic oxychloride, phosphorous oxychloride, zinc chloride, phosphorous pentachloride, calcium acetate, antimonous oxide mixture, antimony pentachloride, antimony pentafluoride, stannous octoate, stannic chloride, diethyl zinc, n-butyl lithium, and mixtures thereof. The catalysts also include Bronsted catalysts such as p-toluene sulfonic acid, nitrobenzene sulfonyl chloride, polyphosphoric acid, cross-linked polystyrene sulfonic acid, acidic silica gel, and mixtures thereof. Other catalysts include basic catalysts such as tetrabutyl titanate, and titanium sodium hydrogen hexabutoxide. The amount of catalyst used is generally about one part catalyst to about 100 parts of the ester monomer. Smaller or larger amounts can also be used, such as 0.0005% to about 0.01% based on the weight of the ester monomer. Usually, the addition of trace amounts of catalyst will provide sufficient catalyst for successfully carrying out the reaction. Optionally, the same catalyst can be used in the transesterification and polycondensation steps, or a different one can be used in each step, for an interrupted or continuous polymerization.

The polymerization optionally can be carried out in the presence of an added inert organic solvent that does not adversely effect the reaction, or the reaction can proceed in the absence of added inert solvent. In the latter embodiment, one of the reactants, for example the polyol monomer, initially serves as the solvent medium. As polymerization proceeds, solvent by-product is removed by distillation, usually with the assist of heat. Solvent also is removed from the reaction vessel either by conventional, continuous, or periodic azeotropic distillation, or the solvent can be distilled under vacuum. Suitable azeotropic solvents are innocuous solvents including toluene, benzene, m-xylene, cumene, pyridine, n-heptane, and the like.

The following examples are set forth as representative methods illustrative of the spirit of the present invention. These examples are not to be construed as limiting the scope of the invention, as these and other functionally equivalent means will be readily apparent to those skilled in the subject art in the light of the present disclosure.

DETAILED DESCRIPTION OF THE EXAMPLES

EXAMPLE 1

To 1 kg of 99+% glycolic acid was added 10 g of antimony trioxide and the reactants reacted at 180° C. with gradual reduction of pressure to 40 mm Hg until all the water had distilled to yield the corresponding polyglycolic acid. Next, the reaction was returned to ambient conditions, the polyglycolic acid isolated, cooled, pulverized and added slowly to a reaction flask heated to 270°–280° C., held at 1 mm Hg to form the glycolide. The glycolide distilled as it formed, yielding 301 g from 355 g of polyglycolic acid. The glycolide was purified by crystallization from isopropanol followed by sublimation at 80° C. and 0.1 mm Hg. The glycolide had a melting point of 82°–83° C., and showed infrared peaks at 1775 cm$^{-1}$ and 1305 cm$^{-1}$.

Next, 9.40 g, 0.081 mole, of glycolide and 1.61 g, 0.026 mole of ethylene glycol were stirred in a closed system at 190° C. for 4 hours to yield the corresponding glycolide—ethylene glycol oligomer. At the end of the reaction, the infrared spectrum showed a shift in the carbonyl band from 1775 cm$^{-1}$ to 1751 cm$^{-1}$ and the disappearance of the band at 1305 cm$^{-1}$. Then, 2.8 g, 1 equivalent based on the ethylene glycol content, of 2,2-diethoxytetrahydrofuran and 10 mg of polyphosphoric acid were added to the glycolide-ethylene glycol oligomer 3:1, Mn 1100, $\overline{M}n(Th)=410$, and the solution stirred at 100° C. with gradual reduction of the pressure to remove the by-product ethanol. Then, the solution was stirred successively at 100° C., 120° C. and 160° C., all at 0.1 mm Hg for a total of 111.5 hours to form the product. During the reaction, gel permeation chromatography of the reaction solution showed Mn values of 1600, 2600 and 3200. The final product had a deep orange color, and a non-tacky film was obtained by compression molding at 100° C. and 15,000 psi for 5 minutes. The reaction sequence leading to the product is illustrated below where x and y are 1 to 10; l is 2 to 6, and n is 10 to 1000:

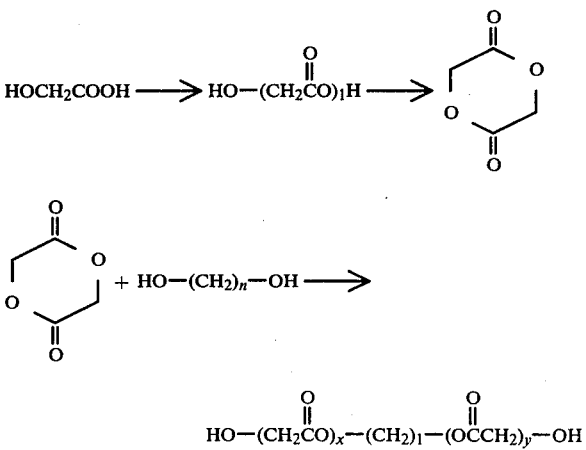

-continued

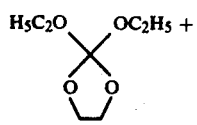

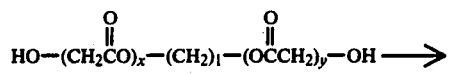

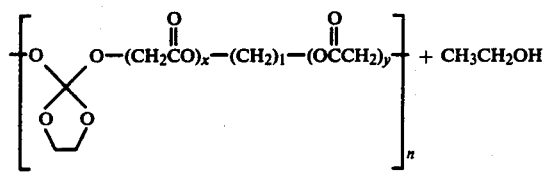

EXAMPLES 2-7

The procedure of Example 1 was repeated herein, with all conditions as previously described except the 2,2-diethoxytetrahydrofuran was replaced by the monomers listed below:
- 2,2-diethoxy-1-oxane;
- 2,2-dipropoxy-1-oxepane;
- 2,2-dibutoxy-1-oxocane;
- 2,2-diethoxy-1,3-dioxolane;
- 2,2-diethenyloxy-1,3-dioxane; and
- 2,2-diethoxy-1,3-dioxonane;

to yield the polymers as follows wherein n is 10 to 1000:

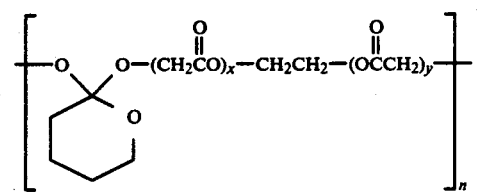

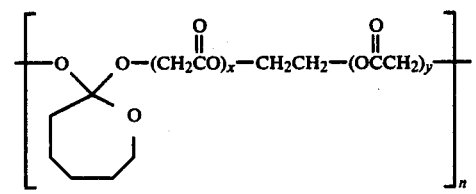

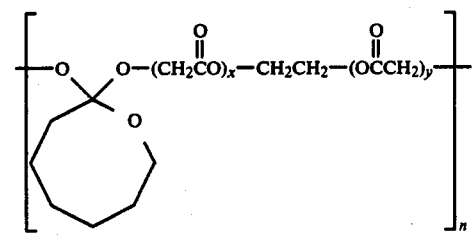

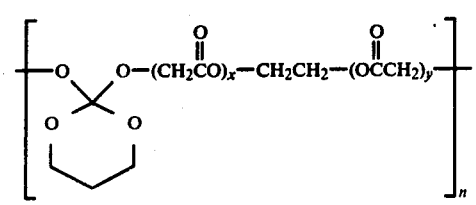

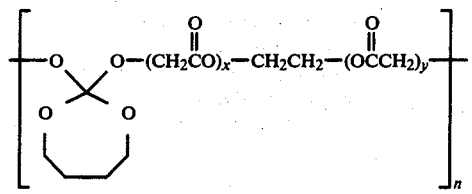

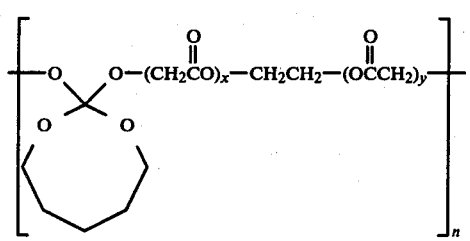

EXAMPLE 8

To 8.14 g, 0.056 mole, of L-lactide and 0.350 g, 0.0056 mole of ethylene glycol was added with stirring 1 mg of lead oxide at 160° C. in a closed system and the reaction carried out for 20 hours. The infrared spectrum of the product, $CHCl_3$ solution, showed a shift in the carbonyl band from 1780 $cm^{-1}$ to 1765 $cm^{-1}$ and a large reduction in the 1250 $cm^{-1}$ band. The lactide-ethylene glycol oligomer 10:1, had a $\overline{Mn}=1300$. Next, the oligomer was polymerized by the polycondensation reaction of Example 1.

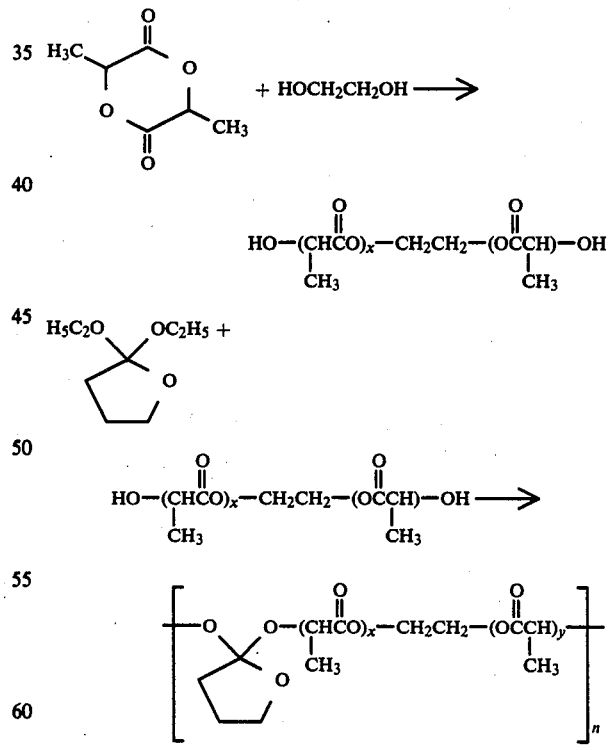

EXAMPLE 9

The procedure of Example 8 was followed in this example, with the addition and reaction of the 2,2-diethoxytetrahydrofuran as follows: 0.9 g of 2,2-diethoxytetrahydrofuran, 1 equivalent based on the ethylene glycol, and 2 mg of polyphosphoric acid were added to the lactide ethylene glycol 10:1 oligomer, 8.5 g, $\overline{M}n=1300$, and the solution stirred at 100° C. under reduced pressure to remove ethanol. Then, the solution was stirred at 100° C. and 0.1 mm Hg, followed by stirring at 140° C. and 0.1 mm Hg to yield the product.

EXAMPLE 10

The procedure of Examples 1 and 9 were followed in the present procedure except for the modification set forth, mainly, 2.7 g of 2,2-diethoxytetrahydrofuran, 1 equivalent based on the diol content, and about 3 mg of polyphosphoric acid were added to glycolide hexamethylene diol, 4:1, oligomer and the solution stirred at 140° C. under reduced pressure to remove ethanol.

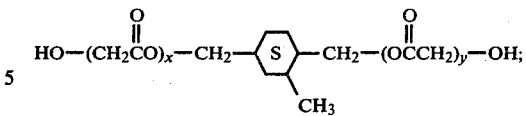

-continued

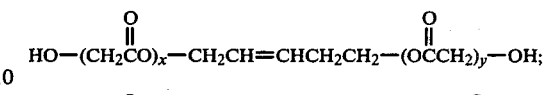

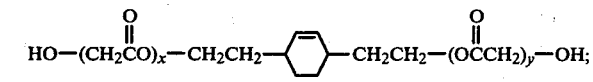

to yield the corresponding polymers:

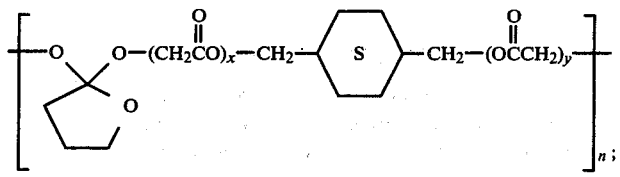

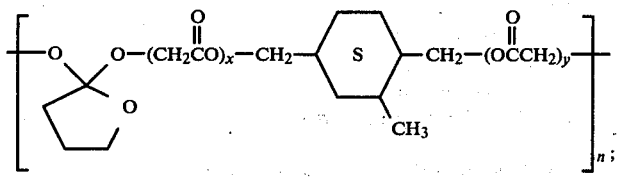

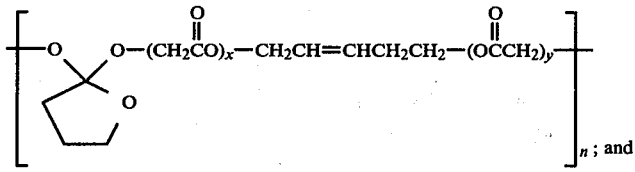

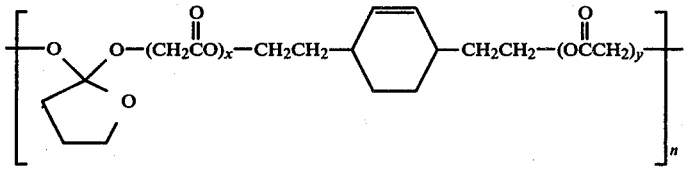

Then, an additional gram of 2,2-diethoxytetrahydrofuran was added and the solution stirred at 180° C. and 0.1 mm Hg for 20 hours to yield the product.

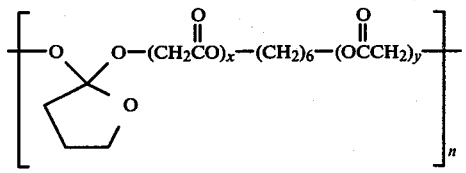

EXAMPLES 11–14

The procedure of Example 10 was repeated in these examples, with all conditions as described except the following oligomers are used for those of the previous example.

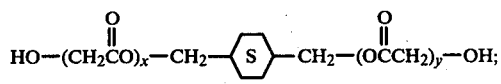

EXAMPLE 15

To 6.8 grams of the glycolide hexamethylene diol (4:1) oligomer of the formula HO—(CH$_2$COO)$_x$—(CH$_2$)$_6$—(OOCH$_2$)$_y$—OH and 2 milligrams of polyphosphoric acid, was added 1.6 grams of 2,2-diethoxytetrahydroforan (1 equivalent as based on the diol content), and the solution heated to 140° C., with reduced pressure to remove the formed alkanol, ethanol. After applying a vacuum of 0.1 mm of Hg for 3 hours at 140° C., the system was equilibrated to atmospheric pressure with nitrogen and 1.0 gram additional of 2,2-diethoxytetrahydrofuran added, and the vacuum cycle repeated. Then, the temperature was raised to 180° C., at 0.1 mm of Hg and the volatiles collected and weighed. During the first 21 hours, 2.1 grams were collected, 0.8 grams during the next 20 hours, and 0.7 grams during the next 30 hours. The volatiles were mainly glycolides by infrared analysis, and the polymer synthesized had the following structure, where n is $10 \times 10^1$ to $10 \times 10^3$:

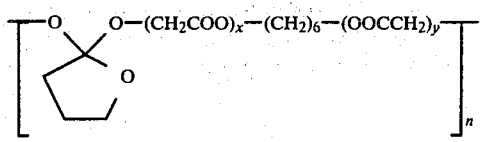

EXAMPLE 16

The procedure of Example 15 is repeated with the oligomer of the formula

used to yield the polymer of the formula:

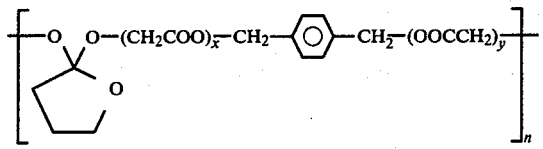

EXAMPLE 17

To 4.56 grams (40.0) mmole of Σ-caprolactone was added 0.59 gram (5.0 mmole) of 1,6-hexamethylene diol and 10 mg of polyphosphoric acid and the mixture heated in a closed system for 2 hours at 180° C. to yield the oligomer. Then, 51.5 grams of Σ-caprolactone hexamethylene diol (8:1) oligomer was added to 8.04 gram of diethoxytetrahydrofuran (1 equivalent based on the diol content of oligomer) and the reactants heated to 125° C. with continuous distillation of ethanol. Next, the reactants were heated to 150° C. and the vacuum pulled to 0.1 mm of Hg. The reactants were reacted under these conditions for 29 hours. Then, at 180° C. and 0.1 mm of Hg for 17 hours. To this was added 1 gram of 2,2-diethoxytetrahydrofuram and the pressure reduction cycle repeated, followed by heating with stirring under nitrogen at 180° C., at 0.1 mm Hg for 16 hours. Finally, an additional 0.5 gram of 2,2-diethoxytetrahydrofuran was added and the cycle repeated to yield the polymer, where x and y are as described, and n is 10 to 1000.

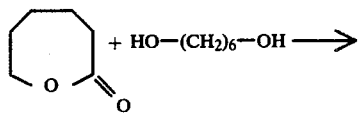

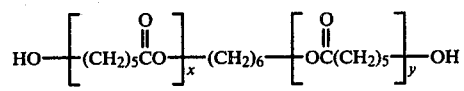

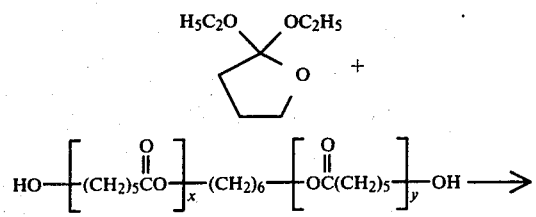

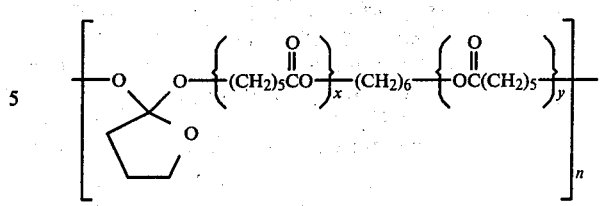

EXAMPLE 18

To 57.5 grams of Σ-caprolactone hexamethylene diol oligomer (24:1) was added 3.2 grams of diethoxytetrahydrofuran (1 equivalent based on the diol content of the oligomer) and the reactants carried through the pressure reduction cycles of Example 17. Then, the reaction solution was heated to 180° C., the pressure reduced to 0.1 mm Hg and the reaction continued for 64 hours with constant stirring. Next, 0.5 gram of 2,2-diethoxytetrahydrofuran was added and the pressure reduction cycle repeated at 180° C. and 0.1 mm Hg for 16 hours. The polymer formed was a light yellow waxy solid, soluble in tetrahydrofuran, and had the depicted structure where x and y are as previously described, and n is 10 to 1000.

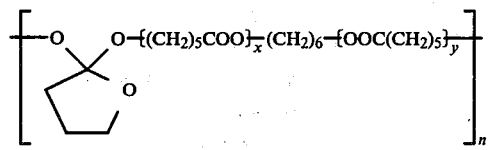

EXAMPLE 19

The procedure of Example 18 is repeated with all conditions as described except the Σ-caprolactone cis-/trans-cyclohexane dimethanol diol is used to yield the following polymer:

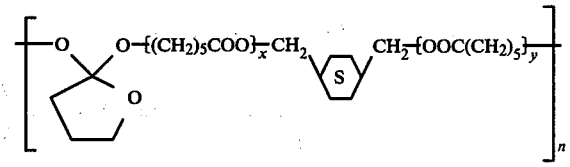

EXAMPLE 20

500 grams of L(+)-lactic acid with 1% zinc oxide was reacted at 140° C. at atmospheric pressure, for ½ hour, with the distillation of water. After most of the water had distilled, vacuum was applied and lactide distilled. The lactide was purified by crystallization from methyl ethyl ketone to give 74 grams of product melting at 95° to 97° C. The lactide had the following structure:

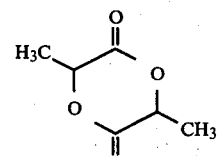

Next, 4.80 grams of lactide and 2.07 grams of ethylene glycol freshly distilled from 1% sodium was stirred at 130° C. for 5 hours. An IR-spectrum in CHCl$_3$ of the product showed a carbonyl band at 1750 cm$^{-1}$ (lactide c=0 absorption: 1780 cm$^{-1}$), and the product distilled at 150° C./0.1 mm Hg. The lactide diol had the structure set forth below where x and y are 1 to 4, R=H or CH$_3$:

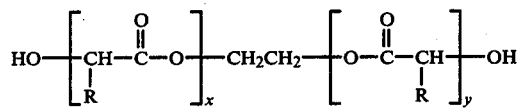

Next, diethoxytetrahydrofuran (1 equivalent based on ethylene glycol content) and polyphosphoric acid (2 mg per g of diethoxytetrahydrofuran) was added to the lactide-glycol adduct. The solution was stirred under N$_2$ at 100° C. and reduced pressure to yield the polymer. The polymer isolated had the structure set forth below wherein R is as defined above:

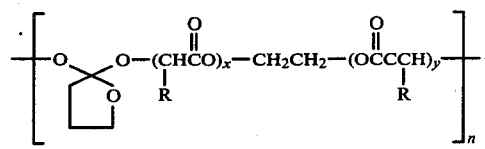

EXAMPLES 21-25

The procedure of Example 20 is repeated in this example with the monomeric pairs as follows:

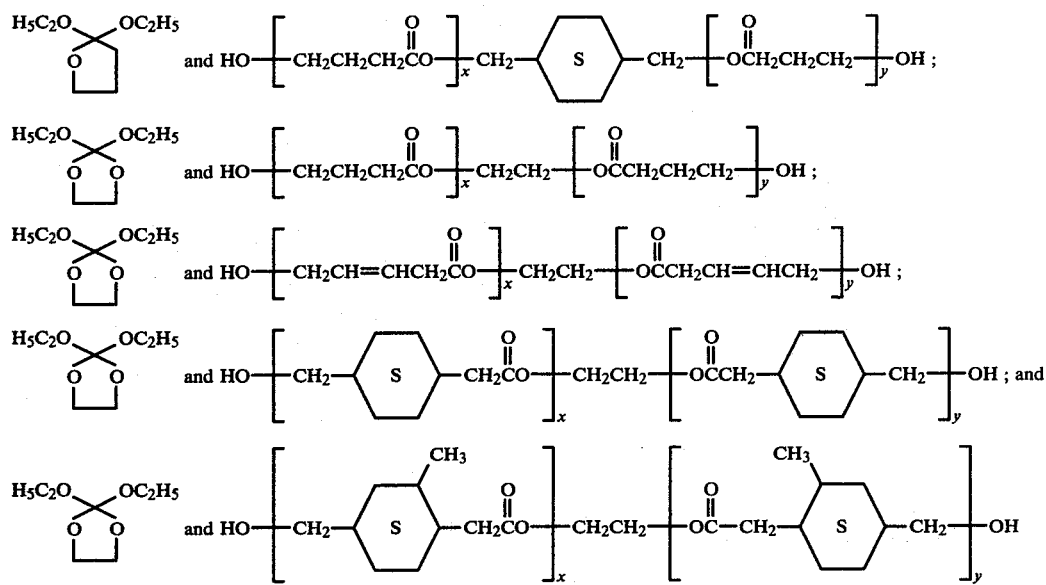

to yield the following polymers:

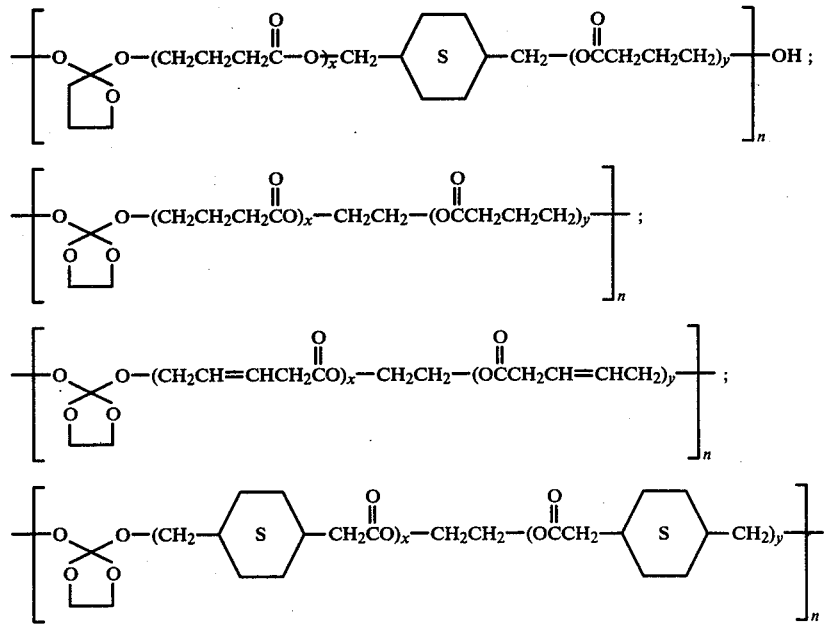

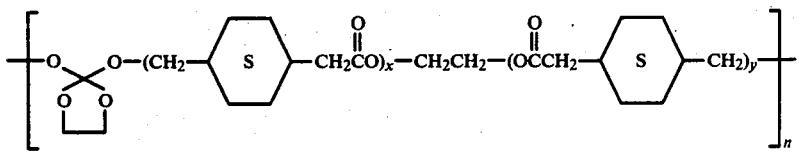

EXAMPLE 26

Into a suitable reaction vessel is added 800 parts of commercially available glycolic acid which is heated to 175°–180° C., at atmospheric pressure to continuously distill off water. Then, the pressure is slowly lowered to the equivalent of 2 mm of Hg and the vessel held at the temperature stated until water ceases to distill. The resultant mixture is then allowed to cool, recovered, and pulverized into a powder. About 560 parts of the latter are slowly added to a flask purged with nitrogen and held at a pressure below the equivalent of 10 mm Hg, and at a temperature from about 275°–285° C. Next, 500 parts of the distillate are dissolved in about 2 times its weight of ethyl acetate at the boiling point, decolorizing charcoal is added, and reflux continued for ½ hour. The solution is filtered while hot, cooled, and pure white crystals of glycolide are recovered on filtering and drying. The recrystallization is repeated twice and 320 parts of glycolide are recovered. The product had a melting point of 83°–84° C., and distinctive infrared spectral bands at 1795 cm$^{-1}$.

The glycolide diol oligomer is prepared by reacting 9.4 g of the glycolide with 1.6 g of ethylene glycol in a closed system for 4 hours. Other oligomers, such as the glycolide hexamethylene diol are prepared by reacting 7.8 g of glycolide with 1,6-hexane diol in a similar manner to yield the oligomer. The oligomers prepared according to the invention are members of a polymeric homologous series with molecular weight of 1000 to 3000. The oligomers can be linear or cyclic and they are used for preparing the high molecular weight polymers of the invention as described in the above examples.

EXAMPLE 27

1,6-hexane diol, 4.42 g, purified by distillation and 2,2-diethoxytetrahydrofuran, 6.0 g, were mixed in a round-bottom flask and thoroughly purged with nitrogen prior to heating. A small amount of p-toluene sulfonic acid, about 1 mg, was added as catalyst. The polymerization was carried out at 130° C. and driven towards product by distilling off ethanol at 130° C. under reduced pressure to yield the polymer poly(2-hexamethylenedioxy tetrahydrofuran). Next, to 5 g of the just prepared polymer was added 2.5 g of terpoly(-glycolic acid-ethylene glycol-2,2-diethoxytetrahydrofuran) in 3:1:1 molar ratio and the reactants heated to 180° C. and reacted under reduced pressure of 0.1 mm Hg for 20 hours. A small amount of crystalline distillate was collected as the polymer formed. The polymer had the following structure wherein x and y are 1 to 20 and m and n are at least 10:

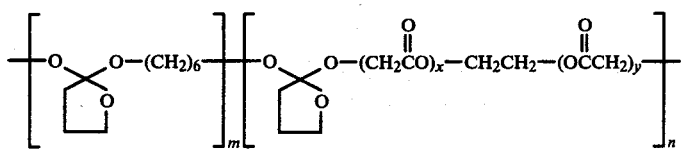

EXAMPLE 28

8.91 g of 1,4-cyclohexane dicarbinol and 10.0 g of 2,2-diethoxytetrahydrofuran were dissolved in 33 ml of toluene, and the mixture heated overnight at 130° C. in the presence of polyphosphoric acid, about 10 mg. Most of the toluene along with by-product ethanol, was removed by slow distillation through a Vigreux column and condenser over this time period. The reaction temperature was next raised to 150° C. and the remaining toluene distilled off. Finally, the Vigreux column was removed and the reaction mixture subjected to vacuum concentration, 0.03 mm Hg, at 160°–170° C. to remove the last trace of solvent and ethanol. The polycondensation yielded the polymer, poly(1,4-cyclohexane dicarbinyl 2,2-dioxytetrahydrofuran). Then, 1.18 g of the just prepared polymer and 4.68 g of terpoly(glycolic acid-1,6-hexamethylene diol-2,2-diethoxytetrahydrofuran) were reacted in a closed system at 180° C. for 72 hours. Then, 1.60 g of 2,2-diethoxytetrahydrofuran and 2 mg of polyphosphoric acid were added and the reaction solution reacted under reduced pressure and 140° C. until the ethanol by-product of reaction had evolved. The polymerization was then completed at 180° C. and 0.1 mm Hg for 16 hours to yield an orange product. Finally, an additional 7.4 g of poly(2,2-dicyclohexyloxy-tetrahydrofuran) was added and the reaction solution reacted at 180° C. and 0.1 mm Hg for 24 hours. The polymer recovered from the reaction had the following structure werein m is 10 to 1000; n is 10 to 1000; and x and y are 1 to 20:

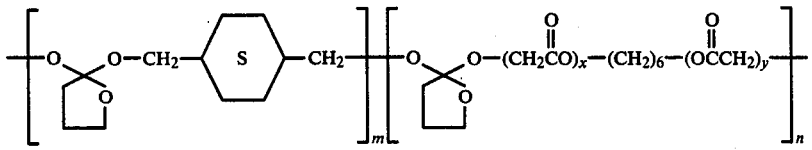

EXAMPLE 29

Repeating the procedure of Example 27, the poly(2,2-dihexamethylene tetrahydrofuran), 5.0 g, was reacted with 5.0 g of terpoly(hexanoic acid-1,6-hexamethylenediol-2,2-diethoxytetrahydrofuran) in 25:1:1 molar ratio, at 180° C. and 0.1 mm Hg for 16 hours, to yield the following polymer:

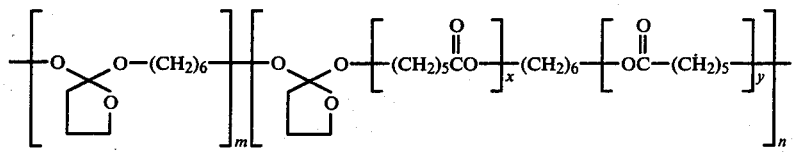

EXAMPLES 30-37

Repeating the procedure of Example 27, the following polymers were prepared where the ratio of the polymer is as stated, B represents block, m and n are 10 to 1000, and x and y are 1 to 100.

DETAILED DESCRIPTION OF INVENTIVE APPLICATIONS

The co- and homopolymers prepared according to the mode and manner of the invention are useful for coating beneficial agents and for making delivery systems shaped as devices that release the agent at a controlled and continuous rate over a prolonged period of time. The phrase "beneficial agent" as used in the speci-

| No. | Ratio | Type | Polymer |
|---|---|---|---|
| 30 | 2:1 | B | 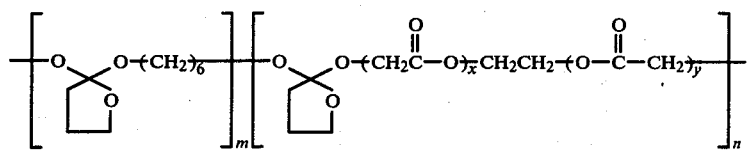 |
| 31 | 1:1 | B | 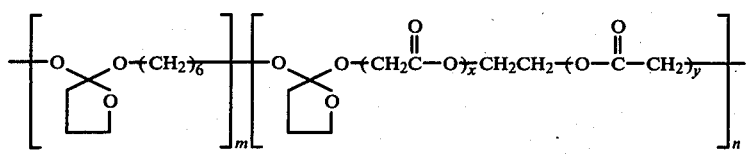 |
| 32 | 2:1 | B | 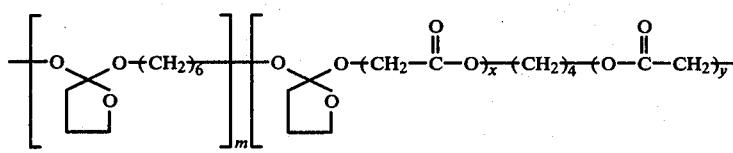 |
| 33 | 1:1 | B | 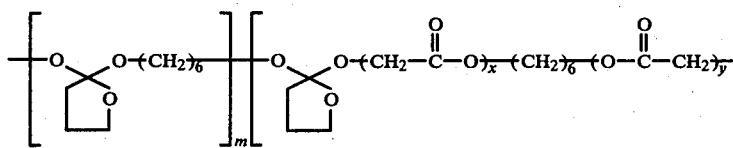 |
| 34 | 1:1 | B | 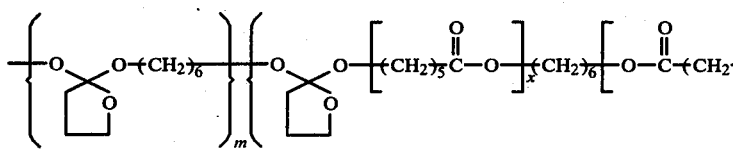 |
| 35 | 2:1 | B | 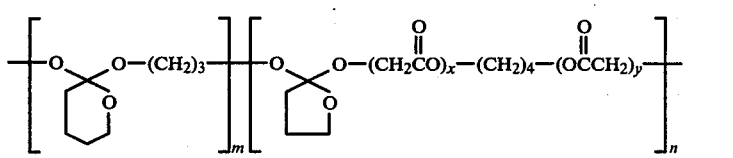 |
| 36 | 3:1 | B | 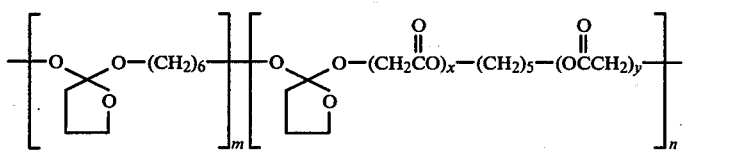 |
| 37 | 2:1 | B | 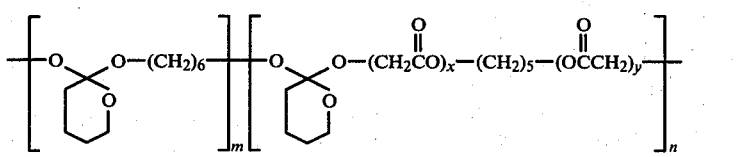 | fication and accompanying claims includes pesticides, herbicides, germicides, biocides, algicides, rodenticides, fungicides, insecticides, plant growth promoters, plant growth inhibitors, preservatives, disinfectants, cosmetics, drugs, plant foods, vitamins, sterilants, plant hormones, fertility inhibitors, fertility promoters, air purifiers, micro-organism attenuators, and nutrients.

The term "drug" as comprehended by beneficial agent, broadly includes physiologically or pharmacologically active substances for producing a localized or systemic effect or effects in animals, including warm blooded animals, mammals, humans and primates, avians, valuable domestic household, zoo, sport or farm animals such as sheep, goats, cattle, horses, etc., or for administering to laboratory animals such as mice, rats and guinea pigs. That is, the co- and homopolymers of the invention can be used for administering drugs that are active at a point in near relation to the delivery site, or, for administering drugs which will produce a response at a site remote from the point of application. The drugs that may be administered include inorganic and organic drugs without limitation, are those drugs that can be transported across a vessel, for example, drugs acting on the central nervous system such as hypnotics and sedatives, narcotic antagonists, psychic energizers, tranquilizers, anticonvulsants, muscle relaxants, anti-parkinson drugs, analgesics, antipyretics, anti-inflammatory, local anesthetics, antispasmodics, anti-ulcer, antimicrobials, antimalarials, antivirals, hormonal, sympathomimetic, cardiovascular, diuretics, antiparasitic, neoplastic, hypoglycemic, essential amino acids, essential elements, and ophthalmic drugs. The above drugs are described in *The Pharmacological Basis of Therapeutics*, edited by Goodman and Gilman, 4th Edition, 1970, published by The Macmillan Company; and in *The Drug, The Nurse, The Patient*, by Falconer, Ezell, Patterson and Gustafson, 5th Edition, 1974, published by W. B. Saunders Company.

The agents can be in various forms, such as uncharged molecules, components of molecular complexes, salts such as hydrochloride, hydrobromide, sulfate, laurates, palmatates, phosphate, nitrate, borate, acetate, maleate, tartrate, oleates, and salicylates. For acidic agents, salts of metals, amines, or organic cations, for example quaternary ammonium, can be employed. Furthermore, simple derivatives such as esters, ethers, and amides which have solubility characteristics compatible with the polymer are suitable for the purpose of the invention. Also, an agent that has limited solubility or is water insoluble can be used in a form that is a water soluble derivative thereof to effectively serve as a solute, and on its release from the polymer it is converted by the environment including enzymes, hydrolyzed by body pH, or metabolic processes to the original form or to an active form. Additionally, agent can be used in co- and homopolymers and devices in various art known forms such as solution, dispersion, paste, cream, particle, granule, emulsions, suspensions and powders.

The co- and homopolymers are useful in a presently preferred embodiment for manufacturing co- and homopolymeric compositions containing drug which composition bioerodes in a biological aqueous environment with an accompanying release of drug. For example, a composition is prepared by heating a co- or homopolymer until it becomes pliable, about 90° C. to 140° C., and then adding micronized hydrocortisone to the polymer. Next, the polymer and the hydrocortisone are thoroughly mixed to produce a good dispersion of the drug, and to yield a 5% hydrocortisone loaded polymer. After the polymer drug formulation cools to room temperature, the formulation can be molded into preselected designed devices that are sized, shaped and adapted for positioning and placement in the environment of use. A formulation containing hydrocortisone can be used for the management of inflammation and bursitis when applied to a drug receptor site.

Other drugs that can be mixed with the co- and homopolymers include ophthalmic drugs selected from the group consisting of pilocarpine, pilocarpine and its therapeutically acceptable salts such as pilocarpine hydrochloride and pilocarpine nitrate, eserine salicylate, atropine sulfate, homatropine and eucatropine; hormonal agents selected from the group consisting of prednisolone, cortisone, cortisol, triamcinolone, $17\beta$-estradiol, ethynyl estradiol, $17\alpha$-hydroxyprogesterone acetate, 19-nor-progesterone, norethindrone, progesterone and other progestational and esterogenic steriods; sympathomimetic drugs selected from the group consisting of epinephrine, amphetamine, ephedrine and norepinephrine; and local anesthetics selected from the group including procaine, lidocaine, naepaine, piperocaine, tetracaine, and dibucane. Generically, the co- and homopolymer agent formulations can contain from about 0.01% to about 40% by weight of agent including drug.

In another embodiment, the co- and homopolymers are useful for coating agents that lend themselves to use as slow release fertilizers. The fertilizers are coated in their conventional form such as granules, powder, beads, particles, and the like. Fertilizers that can be coated include urea, fertilizers with slow ammonia release, fertilizers in the form of water soluble salts such as elements of carbon, nitrogen, phosphorous, sulfur, potassium, calcium, magnesium, manganese, zinc, copper, boron, and the like. Also, fertilizers such as the common fertilizers designated by 8-24-12, 8-8-6, 5-20-20, 12-12-12, 14-16-0, 8-4-6, 3-9-6, and the like. Additionally, the fertilizers or plant nutrient can be impregnated into, or suitably admixed with inert materials such as silica, coke, and the like.

In one embodiment, the co- and homopolymers prepared according to the spirit of the invention are applied to the fertilizers, for example, in granular form, by mixing the fertilizer and the co- and homopolymer in a fluidized bed having a conical bottom. The bed is equipped with an air inlet at the top for introducing air for mixing the polymer and fertilizer until the fertilizer is coated with 0.1% to 10% by weight thereof. The temperature of the air is dependent on the concentration of the dispersion, usually 20° to 100° C. In another embodiment, the fertilizer is coated by mixing the polymer with an organic solvent to facilitate its application in a thin coat to the fertilizer granules. The selection of suitable solvents, in view of those set forth above, is within the skill of the art. The coating compositions can additionally contain pigments, dyes, driers, stabilizers, and the like.

In another embodiment, the co- and homopolymers of the invention are useful for making articles of manufacture including devices releasing beneficial agents. The co- and homopolymers can be processed into articles, including delivery devices, by standard manufacturing techniques. For example, the co- and homopolymers can be extruded into filaments, spun into fibers, pressed into shaped articles, solvent film cast, doctor-bladed into thin films, coated onto an agent by solvent evaporation, coated by using a fluidized bed, compression and transfer molded, and processed by like standard methods of manufacture. The co- and homopolymers of the invention can be used as a single film, in a number of layers made of the same or of different polymers, and they can be made into devices of various geometric shapes, for example flat, square, round, tubular, disc, ring, and the like. Also, the devices of the invention are sized, shaped and adapted for implantation, insertion or placement on the body, in body cavities and passageways, or for positioning in other environments of use, for example, streams, aquariums, fields or reservoirs. Standard procedures for processing polymers are described in *Plastic Encyclopedia*, Vol. 46, pages 62 to 70, 1969. The co- and homopolymers of the invention are useful for making devices for dispensing a beneficial agent, as they have a controlled degree of hydrophobicity in the environment of use and because they erode into innocuous products at a continuous rate which exhibits no known deleterious effects on the environment or towards an animal body.

While the invention pertains to co- and homopolymers, and while these polymers and the method for making them have been described in detail for the now preferred embodiments, those skilled in the art will appreciate that various modifications, changes, additions and omissions in the invention can be made without departing from the spirit of the invention.

I claim:

1. A composition of matter comprising a homopolymer of the general formula:

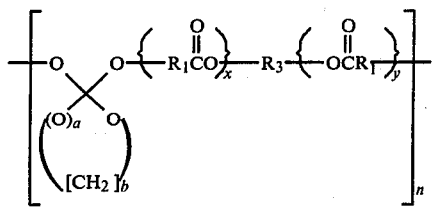

wherein $R_1$ is a member selected from the group consisting of alkylene of 1 to 10 carbons; alkenylene of 2 to 10 carbons; cycloalkylene of 3 to 7 carbons; cycloalkylene of 3 to 7 carbons substituted with a member selected from the group consisting of an alkyl of 1 to 10 carbons; alkenyl of 2 to 10 carbons, alkoxy of 1 to 10 carbons and alkylene of 1 to 10 carbons; cycloalkenylene of 5 to 7 carbons; cycloalkenylene of 5 to 7 carbons substituted with a member selected from the group consisting of an alkyl of 1 to 10 carbons, alkenyl of 2 to 10 carbons, alkoxy of 1 to 10 carbons and akylene of 1 to 10 carbons; arylene, arylene of 6 to 20 carbons substituted with an alkyl of 1 to 10 carbons, alkenyl of 2 to 10 carbons, alkoxy of 1 to 10 carbons and alkylene of 1 to 10 carbons; $R_3$ is the same as $R_1$, a is 0 to 1, b is 2 to 6, n is 10 to 1000, ans x and y are 0 to 100 with at least one of x and y at least one, a drug dispersed in said homopolymer, and wherein the drug is released in a therapeutically effective amount at a controlled rate to an environment of use as the homopolymer erodes when in the environment over a prolonged period of time.

* * * * *

UNITED STATES PATENT OFFICE
CERTIFICATE OF CORRECTION

PATENT NO. : 4,155,992
DATED : May 22, 1979
INVENTOR(S) : Edward E. Schmitt

It is certified that error appears in the above-identified patent and that said Letters Patent are hereby corrected as shown below:

In column 4, line 30, the formula

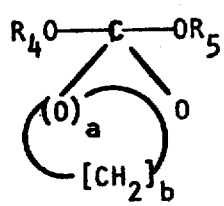 should read 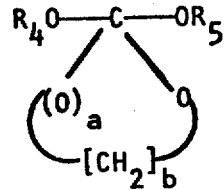

In column 5, line 55, the formula

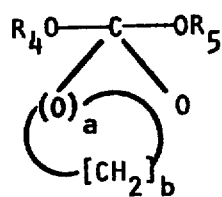 should read 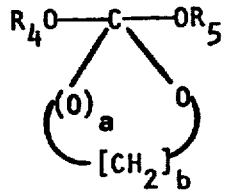

Signed and Sealed this

Twentieth Day of November 1979

[SEAL]

Attest:

RUTH C. MASON
Attesting Officer

LUTRELLE F. PARKER
Acting Commissioner of Patents and Trademarks